(12) United States Patent
Hörnig

(10) Patent No.: US 7,600,280 B2
(45) Date of Patent: Oct. 13, 2009

(54) PATIENT TABLE

(75) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 234 days.

(21) Appl. No.: 11/348,774

(22) Filed: Feb. 7, 2006

(65) Prior Publication Data

US 2006/0174412 A1 Aug. 10, 2006

(30) Foreign Application Priority Data

Feb. 7, 2005 (DE) ............. 10 2005 005 605

(51) Int. Cl.
*A47B 23/02* (2006.01)
(52) U.S. Cl. .................. 5/507.1; 5/600
(58) Field of Classification Search .......... 5/507.1, 5/524, 658
See application file for complete search history.

(56) References Cited

U.S. PATENT DOCUMENTS

| | | | | |
|---|---|---|---|---|
| 1,649,053 A | | 11/1927 | Allison | |
| 2,644,961 A | * | 7/1953 | Hillenbrand et al. | 5/507.1 |
| 5,522,098 A | * | 6/1996 | Podgorschek | 5/602 |
| 5,884,350 A | * | 3/1999 | Kurze | 5/600 |
| 6,209,463 B1 | * | 4/2001 | Koharchik et al. | 108/7 |
| 6,550,084 B2 | * | 4/2003 | Siepmann et al. | 5/507.1 |
| 6,684,419 B1 | | 2/2004 | Perla | |
| 2003/0014817 A1 | * | 1/2003 | Gallant et al. | 5/600 |
| 2004/0177445 A1 | * | 9/2004 | Osborne et al. | 5/600 |

* cited by examiner

*Primary Examiner*—Peter M. Cuomo
*Assistant Examiner*—William Kelleher

(57) ABSTRACT

In order to make it possible for a patient to easily and safely mount a patient table in a manner which requires little effort, at least one, especially extendable and retractable and/or fold-up and fold-down step is integrated into a patient mounting aid in the inventive patient table. In the inventive method there is provision for the at least one step initially to be extended and/or folded down, then for a beginning of the examination to be automatically determined and finally for the at least one step to be retracted and/or folded up again, depending on the determination of the beginning of an examination.

4 Claims, 3 Drawing Sheets

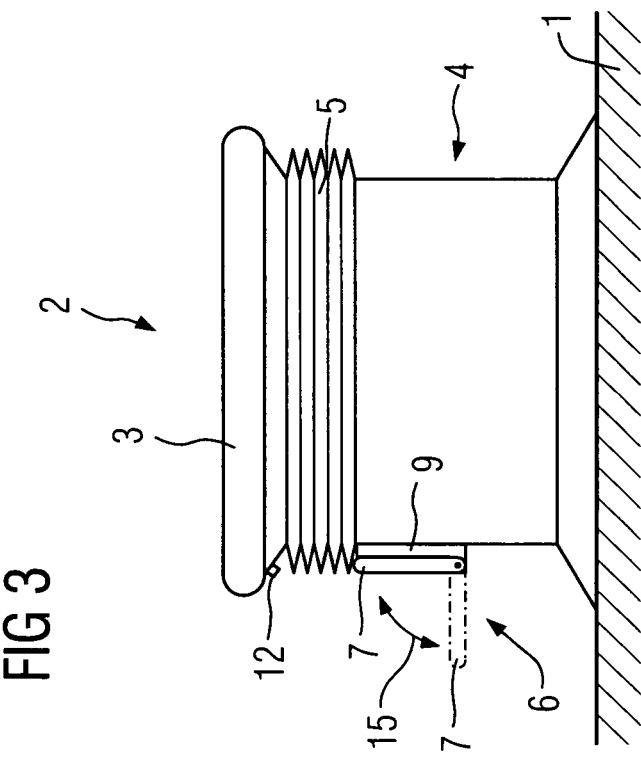
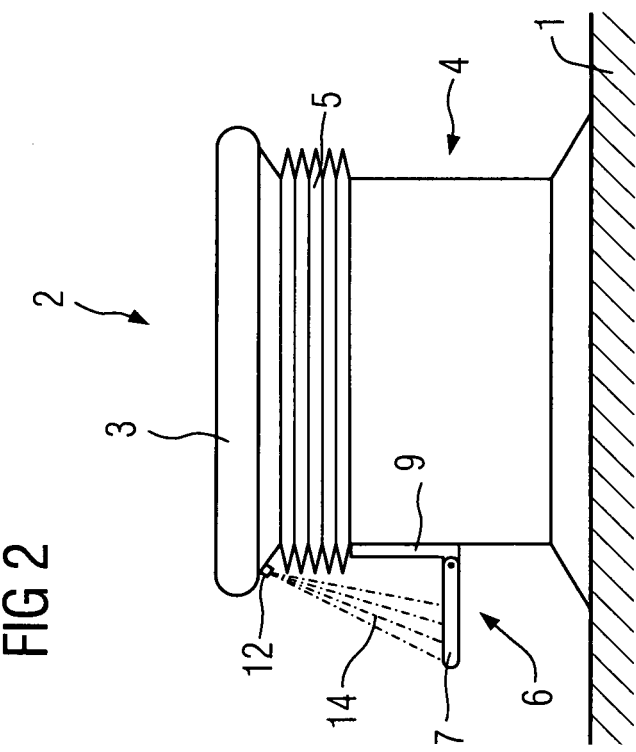

PATIENT TABLE

CROSS REFERENCE TO RELATED APPLICATIONS

This application claims priority to the German application No. 10 2005 005 605.9, filed Feb. 7, 2005 which is incorporated by reference herein in its entirety.

FIELD OF INVENTION

The invention relates to patient table as well as to a method for its control.

BACKGROUND OF INVENTION

For many examinations, especially for many radiological examinations, there is provision for positioning a patient to be examined on a patient table. The patient table usually features a table foot and a patient support arranged on this table foot. Provided the patient can do so without outside aid, it is generally desirable for them to position themselves on the patient support. This is often prevented by the patient table being too high for the patient concerned.

SUMMARY OF INVENTION

Patient tables, especially for radiological systems, are generally known which provide height-adjustable patient supports. For height adjustment a mechanical or hydraulic system is provided in the table foot which, by virtue of its construction, prevents the patient bed from being lowered beyond a relevant minimum height. This minimum height is still too high for many patients to climb onto the patient table unaided.

An object of the present invention is to specify a patient table as well as a method for its control so as to give the patient a simple and safe way of getting onto the patient table with little effort.

This object is achieved by the claims. Advantageous embodiments are the object of the associated independent claims.

The at least one step integrated into the patient mounting aid for the patient table makes it possible for the patient to climb onto the patient table themselves in a manner which both requires little effort and is convenient for them, and thereby to position themselves on the table's patient support for an examination without outside assistance. Integrating a patient mounting aid into the patient table—in the sense of attaching the patient mounting aid to the structure of the patient table—guarantees that it is immediately available to the patient if required. The term "step" is intended to be understood here and below as a step on which a person—in this case the patient—can tread.

So that particularly little effort is required, and to make it convenient for the patient, the patient mounting device is arranged on a table foot, especially one designed for height adjustment of the patient table.

In accordance with an advantageous embodiment of the invention there is provision for the at least one step to be able to be extended and retracted and/or folded down and folded up. This makes it possible to only extend and/or fold down the step for the patient when required and to retract it or fold it up during the examination of the patient to save space.

For ease of handling there is provision for an external power-operated drive, especially in the form of an electric motor, for power-operated extension and retraction and/or folding down and folding up of the at least one step. In addition this power-operated external drive creates the prerequisite for the control of the automatic extension or retraction and/or folding down or folding up of the step described below.

In accordance with an advantageous embodiment of the invention there is provision for an opposing force measurement means for automatic deactivation of the external power-operated drive depending on this opposing force against the extension or retraction and/or folding down or folding up. This makes it possible, so as to avoid the danger of injury to the patient or to an operator, to interrupt an external power-operated movement of the at least one step if the patient or the operator exerts a force against this movement, with a foot or with a leg for example. This especially prevents the step being retracted or folded up while the patient is standing on it or is within its area of movement.

To further simplify the ease of handling of the mounting aid for a user, in accordance with further advantageous embodiments of the invention, three types of sensor described in more detail below—a patient support sensor, a load sensor and a free space sensor—are provided, through which individually in each case—or through an especially advantageous combination of these sensors—a potential beginning of an examination can be determined on the basis of a completed positioning of the patient on the patient support for control of an automatic retraction and/or folding-up of the at least one step.

For simple and safe control of the automatic retraction and/or folding-up, at least one patient support sensor, especially arranged on a patient support or on the table foot, is provided, through which a positioning of a patient on the patient bed can be determined. This can be determined particularly easily with the aid of the at least one patient support sensor in form of at least one pressure sensor integrated into the patient support or into the table foot, but with use of patient support sensors based on an optical or inductive measurement method also being conceivable. With a height-adjustable patient table the patient support sensor can for example also be arranged in the mechanical or hydraulic system provided in the table foot for height adjustment. Usefully the at least one step is only retracted or folded up if the patient is completely positioned on the patient table, as can be determined for example with reference to a force exerted on the patient table which corresponds to the relevant body weight of the patient.

For especially simple and, in the sense of avoiding the danger of injury for a patient of for the operator, safe control, at least one load sensor, especially arranged on the patient mounting aid, is provided, through which a load on the at least one step and thus indirectly also a positioning of the patient on the patient support can be determined it is worthwhile in this case only to retract and/or fold down the at least one step if there is no load being exerted on it at all, since this removal of the load indicates that the patient has finished climbing up onto the patient table and has positioned himself on its patient support.

For especially secure recording of the intermediate area between the least one step on the one hand and the patient support on the other hand and/or the area of movement of the least one step which goes beyond determining the load on the step, at least one free space sensor is provided through which the free space in the intermediate area and/or the area of movement and thus indirectly a positioning of the patient on the patient support can be determined. At least one of free space sensor is embodied especially simply in the form of at least one light barrier, but with other sensors, for example ultrasound sensors or infrared displacement measurement sensors, also being conceivable as free space sensors. Expediently the at least one step it is only retracted and/or folded up if the intermediate area and/or the area of movement are free and the patient is thus positioned on the patient support.

The positioning can be recorded particularly reliably on the basis of a chronological sequence of the pressure on the patient support or the load on the step or of the free space in the intermediate area. For the mounting and the positioning of the patient these three parameters—pressure, step load and free space—each exhibit a characteristic sequence. For example, when mounting the patient table the patient will initially exert pressure on the least one step with at least one foot and subsequently, on reaching the patient support, will release the pressure again. By taking into account a number of parameters in a chronological sequence it is possible to further improve the reliability for determining the positioning. For example a positioning on the patient support can only be assumed if initially a load is placed on the step and then a load is subsequently removed, after the removal of this load from the step the intermediate space is free and in addition pressure is exerted on the patient support.

The actual start of the examination is determined simply and safely on the basis of operation of the least one device used for the examination.

In accordance with an advantageous embodiment of the invention there is provision for extending and retracting and/or folding up or folding down the step depending on determination of the start of an examination under timer control, especially after a time delay. To guarantee additional safety when the patient mounts the table, the start of an examination can be determined initially on the basis of the parameters given above for example and there can be delayed retraction and/or folding up of the at least one step after a specific time interval relative to the beginning of this examination. This makes it possible for the patient, after reaching the patient support, to safely dismount from the patient table within this time interval with the aid of the at least one still extended and/or folded down step, for example for the purpose of repositioning himself.

Especially conveniently the extension and/or the folding down is performed automatically, depending on the end of the examination, based on an operation of the at least one device used for the examination.

BRIEF DESCRIPTION OF THE DRAWINGS

The invention, as well as further advantageous embodiments of the invention in accordance with features of the subclaims, are explained in greater detail below with reference to schematic diagrams of exemplary embodiments in the drawing, without this restricting the invention to this exemplary embodiment in any way; The Figures show:

FIG. 2 a side view of the patient table from FIG. 1;

FIG. 3 a side view of the patient table from FIG. 2 with the step in a folded-up position;

DETAILED DESCRIPTION OF INVENTION

Figure 1:
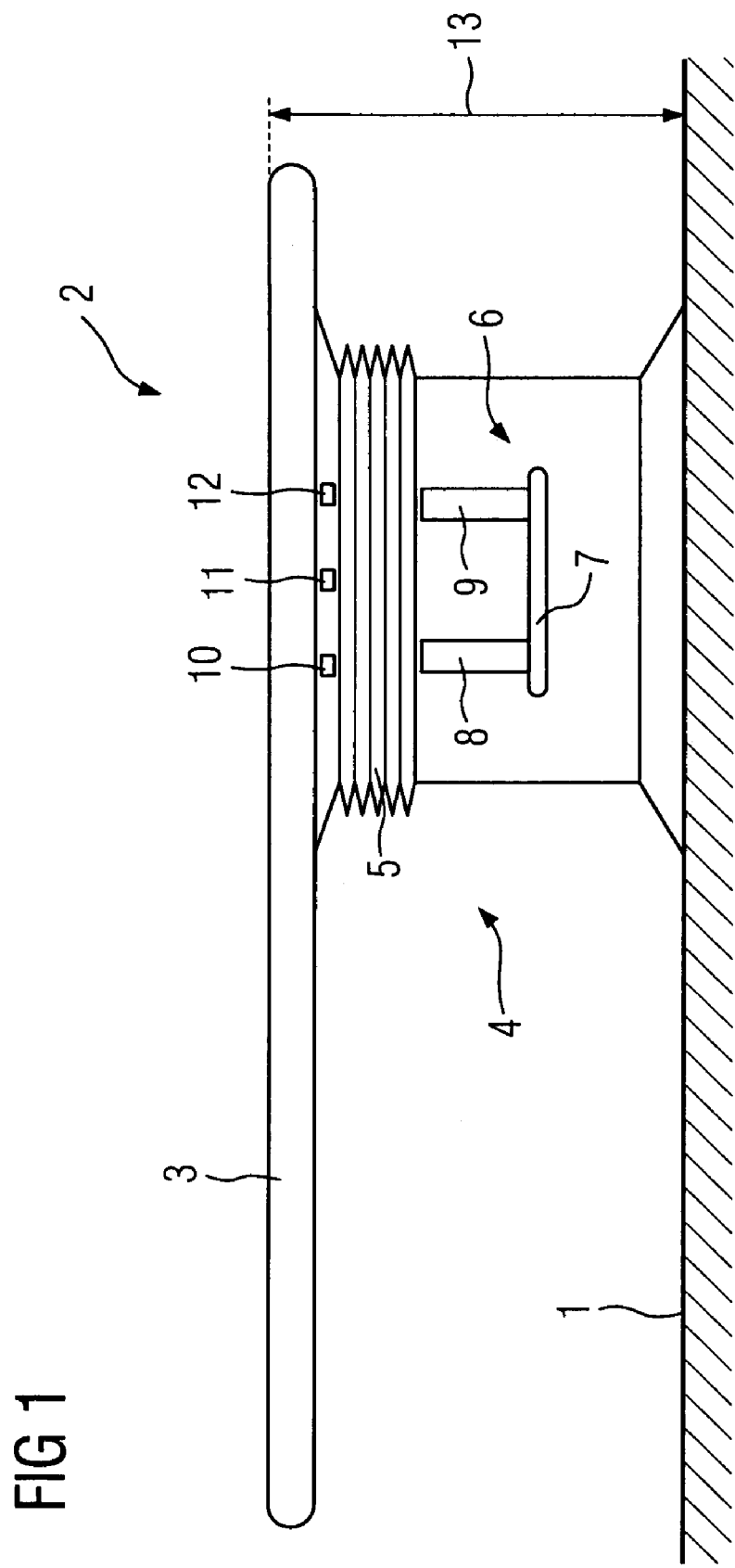
FIG. 1 a front view of the patient table with a patient mounting aid with its single step folded down.

FIG. 1 shows a front view of a patient table 2 placed on a floor surface 1 consisting of a patient support 3 and a height-adjustable table foot 4 with a support part 5 that can be raised and lowered, with a patient mounting aid 6 with a step 7 which can be folded up and down additionally attached by two brackets 8, 9 and with three light barriers 10-12 above it. To allow the patient to mount the patient table 2 the table is set to its minimum height 13 and the step 7 is folded down.

FIG. 2 shows a side view of the patient table 2 from FIG. 1.

The light barriers 10-12 are intended, with the aid of light beams 14 sent out by them and reflected back to them by reflectors on the step 7, to determine a free space in the intermediate area between the patient support 3 on the one hand and the step 7 on the other hand, with the step 7 only being folded up if this intermediate area is free.

Pressure sensors which determine a positioning of the patient on the basis of a force 2 exerted by the latter on the patient support are arranged integrated into the patient support 3 or into the table foot 4, with the step 7 only being retracted if a constant pressure on the patient support 3 indicates that positioning has been completed.

In addition a load sensor for determining a load exerted by the patient on the step 7 is provided on the patient mounting aid 6, with the step 7 only being folded up if a release of the step load indicates that the patient has left the step 7.

FIG. 3 shows the patient table 2 from FIG. 2, with the step 7 being folded up from an initial position 16 indicated by a dotted and dashed line by an external power-operated drive through a folding movement in direction 15. It is useful to undertake an examination of the patient with a step 7 folded up in this manner and after the end of the examination to fold this step back down again into the initial position 16 using an external power-operated drive, so that after the examination the patient can dismount from the patient table easily and safely again.

Figure 4:
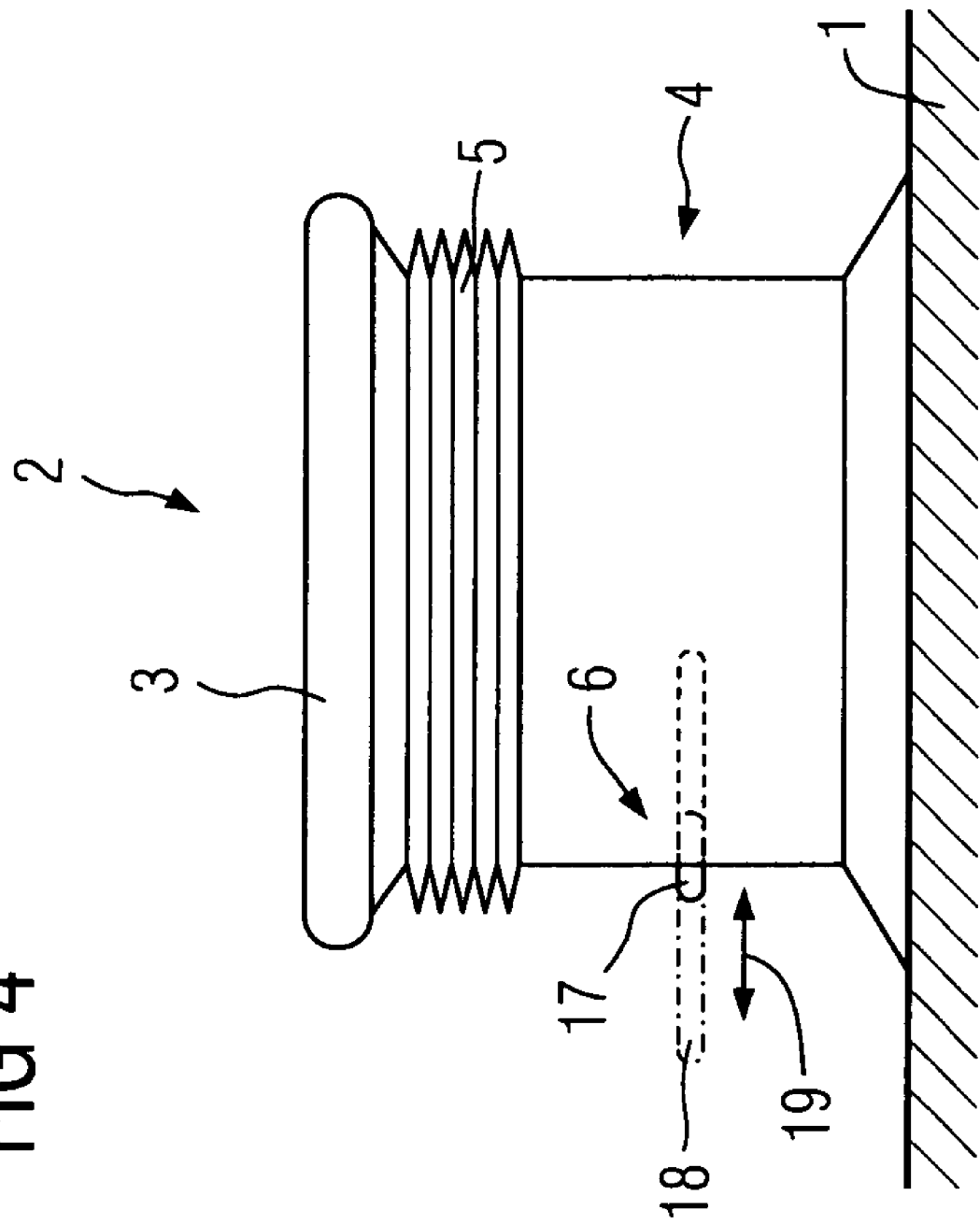
FIG. 4 a side view of a patient table in accordance with FIG. 2 with a patient mounting aid in which the step can be extended and retracted.

FIG. 4 shows a patient table 2 as shown in FIG. 3, with in this exemplary embodiment the step 17 being able to be extended or retracted in direction 19 by means of an external power-operated drive. The position 18 of the extended step 17 is shown by a dotted and dashed line and the part of the retracted step 17 in the patient table foot is indicated by a dashed line.

In order up to detect an obstacle, e.g. a leg of the patient, in the area of movement of the step at 17 when the step 17 is being extended by an external power-operated drive, which corresponds in this diagram to the extended position of step 17 and if necessary to be able to interrupt the extending operation, an opposing force measurement means is provided on the patient mounting aid 6. In this exemplary embodiment it would be possible to embody this opposing force measurement means in the form of a switch arranged on the end face of the step 17 in the direction of extension which is activated by coming into contact with an obstacle and thereby initiates an interruption of the external power-operated drive.

The invention can be summarized as follows: In order to make it possible for a patient to easily and safely mount a patient table in a mariner which requires little effort, in the inventive patient table at least one, especially extendable and retractable and/or fold-up and fold-down step is integrated into a patient mounting aid. In the inventive method there is provision for the at least one step initially to be extended and/or folded down, then for the beginning of the examination to be automatically determined and finally for the at least one step to be retracted and/or folded up again depending on the determination of the beginning of the examination.

The invention claimed is:

1. A patient table, comprising a patient support; a table foot under said patient support and integral to the patient table; and a boarding device arranged on the table foot, the boarding device having at least one extendable and retractable and/or foldable step for supporting a patient to get on the patient table; a power-operated drive for extending and retracting and/or folding the at least one step responsive to positioning of a patient on the patient support and/or operation of an examination device;

at least one patient support sensor for controlling the retracting or folding based upon a position of the patient on the patient table detected by the patient support sensor;

at least one load sensor for controlling the retracting or folding based upon a step load detected by the load sensor; and at least one space sensor on the patient table for controlling the retracting or folding based upon a free space in an intermediate area between the at least one step and the patient support, or in an area of movement related to the at least one step;

wherein upon being extended and/or unfolded, the at least one step retracts and/or folds when a patient is sensed by the patient support sensor after load on the at least one load sensor is removed and the intermediate area or in the area of movement is free as sensed by the at least one space sensor.

2. The patient table in accordance with claim 1, further comprising an opposing force measurement device for automatically deactivating the external power-operated drive, the deactivation based upon an opposing force detected by the opposing force measurement device, the opposing force directed against the extending and retracting and/or folding.

3. The patient table in accordance with claim 1, wherein the patient support sensor is a pressure sensor.

4. The patient table in accordance with claim 1, wherein the space sensor comprises at least one light barrier.

\* \* \* \* \*